(12) United States Patent
Smyj et al.

(10) Patent No.: US 7,060,831 B2
(45) Date of Patent: Jun. 13, 2006

(54) PROCESS FOR THE PREPARATION OF TETRAHYDROTHIENO[3,2-C] PYRIDINE DERIVATIVES

(75) Inventors: Robert P. Smyj, Brantford (CA); Gamini Weeratunga, Brantford (CA)

(73) Assignee: Apotex Pharmachem Inc., Brantford (CA)

( * ) Notice: Subject to any disclaimer, the term of this patent is extended or adjusted under 35 U.S.C. 154(b) by 0 days.

(21) Appl. No.: 10/774,506

(22) Filed: Feb. 10, 2004

(65) Prior Publication Data
US 2005/0137401 A1    Jun. 23, 2005

(30) Foreign Application Priority Data
Dec. 23, 2003   (CA) .................................. 2454015

(51) Int. Cl.
C07D 471/02    (2006.01)
C07F 7/04    (2006.01)
C07F 7/08    (2006.01)

(52) U.S. Cl. ....................... 546/114; 546/114; 556/465; 556/489

(58) Field of Classification Search ................ 546/114; 556/465, 489
See application file for complete search history.

(56) References Cited

U.S. PATENT DOCUMENTS

| 4,051,141 A | 9/1977 | Castaigne ................. 260/294.8 |
| 4,127,580 A | 11/1978 | Braye ......................... 546/114 |
| 4,529,596 A | 7/1985 | Aubert et al. ................ 514/231 |
| 4,847,265 A | 7/1989 | Badorc et al. .............. 514/301 |
| 6,495,691 B1 | 12/2002 | Horne et al. ................ 546/114 |

FOREIGN PATENT DOCUMENTS

FR    2424278    4/1978 ..................... 495/4

OTHER PUBLICATIONS

"Steps for Troubleshooting a Process", Practical Process Research & Development, by Anderson, N.G., Academic Press, 2000, p. 323-324.
"Benzylation via Tandem Grignard Reaction—Iodotrimethylsilane (TMSI) Mediated Reduction", Tetrahedron, 1995, vol. 51, No. 41, p. 11043-11062.
"Synthetic Methods and Reactions. 621 Transformations with Chlorotrimethylsilane/Sodium Iodide, a Convenient in Situ Iodotrimethylsilane Reagent", J. Org. Chem., 1979, vol. 44, No. 8, p. 1247-1251.

Primary Examiner—D. Margaret Seaman
Assistant Examiner—Niloofar Rahmani
(74) Attorney, Agent, or Firm—Samuel Tekie; Ivor M. Hughes; Marcelo K. Sarkis

(57) ABSTRACT

A process for the preparation of tetrahydrothieno[3,2-c] pyridine compound of formula 6:

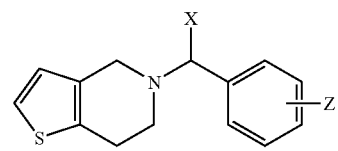

or their pharmaceutically acceptable salts, wherein the meaning of X is carboxyl, alkoxycarbonyl, aryloxycarbonyl, or carbamoyl of formula

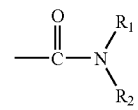

wherein $R_1$ and $R_2$ can be individually or simultaneously hydrogen, alkyl or part of a heterocyclic structure; Z can be hydrogen, halogen, alkyl, aryl, aryloxy or alkoxy group, the process comprising conducting a dehydroxylation reaction on the compound of formula 5 in order to obtain a compound of formula 6, wherein said dehydroxylation reaction is effected by iodosilane represented by the formula $Si(R_3)_3I$, wherein $R_3$ selected from an alkyl, alkenyl, alkynyl, aromatic group, or combinations of thereof

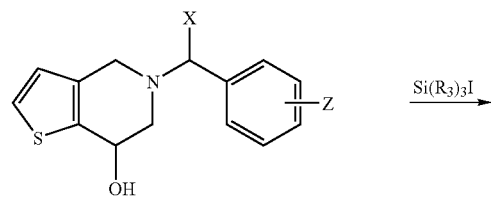

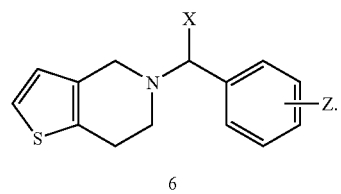

13 Claims, No Drawings

PROCESS FOR THE PREPARATION OF TETRAHYDROTHIENO[3,2-C] PYRIDINE DERIVATIVES

FIELD OF INVENTION

The present invention relates to a novel process for the preparation of tetrahydrothieno[3,2-c]pyridine derivatives, in particular to a racemic or enantiomerically enriched 4,5,6,7-tetrahydrothieno[3,2-c]pyridines and pharmaceutically acceptable salts thereof.

BACKGROUND OF THE INVENTION

The dextrorotatory enantiomer (Structure 1), bearing the International Non-Proprietary name Clopidogrel, has the absolute configuration S and is a commercially significant drug with antithrombic and platelet aggregation inhibiting activity as disclosed in U.S. Pat. No. 4,847,265. Similar properties are disclosed in U.S. Pat. No. 4,529,596.

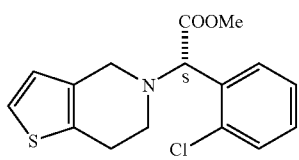

1

Structure 2, known as Ticlopidine, is an antithrombotic drug with platelet aggregation inhibiting properties as disclosed in U.S. Pat. No. 4,051,141 and U.S. Pat. No. 4,127,580.

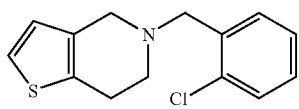

2

The synthesis of Ticlopidine is described in Heterocycles, 1979, 12, 1479 and in FR Pat. 2,424,278. A final step towards Ticlopidine involves the dehydroxylation of hydroxyl precursor 3 (R=H) with $SnCl_2$/HCl reagent (Scheme 1). This reagent has also been applied towards the synthesis of Clopidogrel (R=COOCH$_3$). (U.S. Pat. No. 6,495,691).

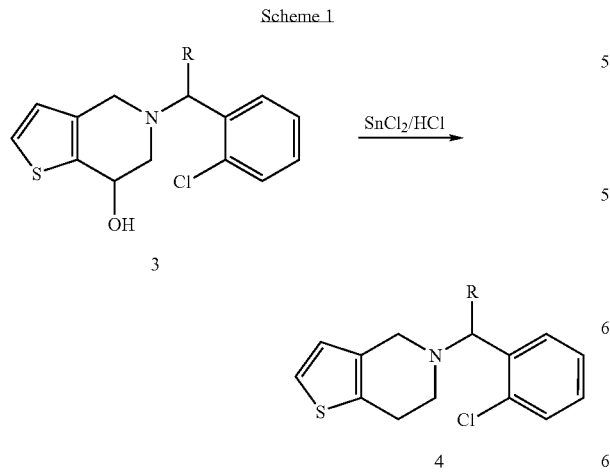

Scheme 1

Enormous difficulties exist for using $SnCl_2$ in this type of transformation especially when considering large scale reactions. The main problem consists of removing the tin byproducts after completion of the reaction. In our experience, from laboratory scale reactions, an aqueous work-up of the reaction results in the formation of persistent emulsions. This would result in increased processing time particularly on scale-up to achieve phase separations. Emulsions are very problematic on scale-up and need to be avoided in commercial production of pharmaceuticals and fine chemicals (see Practical Process Research & Development, by Anderson, N. G., Academic Press, 2000, pages 323–324). Furthermore, the possibility of tin contamination in the final product exists. Therefore, it would be very difficult to meet the high purity specifications required for a pharmaceutical product. Consequently, a method that would not suffer from the disadvantages of the prior art was required.

It is therefore an object of the present invention to provide an improved process for the preparation of racemic and/or enantiomerically enriched 4,5,6,7-tetrahydrothieno[3,2-c] pyridines with inexpensive reagents and which avoids the problems encountered with the $SnCl_2$/HCl reagent (i.e. work-up and isolation of product).

SUMMARY OF THE INVENTION

The present invention provides for an improved and novel process for the preparation of racemic and/or enantiomerically enriched 4,5,6,7-tetrahydrothieno[3,2-c]pyridines of general formula 6 from 7-hydroxy-4,5,6,7-tetrahydro-5-thienol[3,2-c]pyridines of general formula 5 (Scheme 2) by employing iodosilanes represented by the formula $Si(R_3)_3I$, for example iodotrimethylsilane (TMSI), as a dehydroxylation reagent.

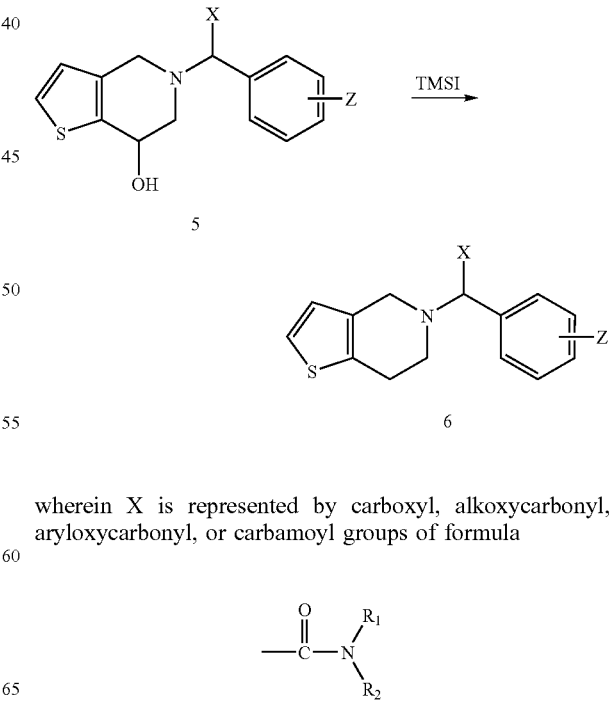

Scheme 2 wherein X is represented by carboxyl, alkoxycarbonyl, aryloxycarbonyl, or carbamoyl groups of formula wherein $R_1$ and $R_2$ can be individually or simultaneously hydrogen, alkyl or part of a heterocyclic structure; Z can be hydrogen, halogen, alkyl, aryl, aryloxy or alkoxy group; $R_3$ may be an alkyl, alkenyl, alkynyl, aromatic group, or combinations of thereof. The process of this invention also includes when compound 5 is in either free base form or various salt forms. The reaction may be conducted in polar aprotic solvents (e.g. acetonitrile, $CH_2Cl_2$, or N,N-dimethylformamide), and in aromatic solvents such as toluene or equivalent thereof, or in various combinations of the aforementioned solvents.

The use of TMSI as a reducing agent was illustrated in Tetrahedron, 1995, 51, 11043 involving the dehydroxylation of biarylmethanols such as 7 to form the biarylmethane 8 (Scheme 3).

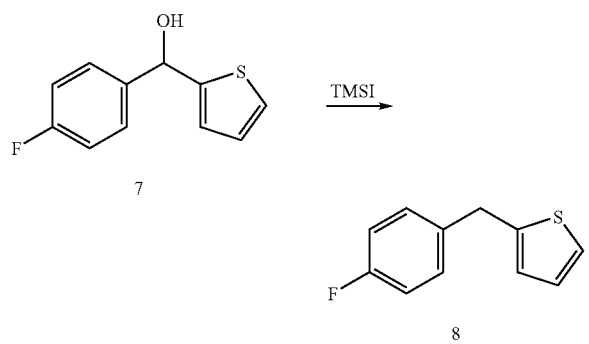

Scheme 3

7

8

Furthermore, TMSI is known to cleave methyl esters (J. Org. Chem., 1979, 44, 1247) and is viewed as an unselective reagent when employed in reactions involving substrates possessing both benzylic alcohol and ester functional groups. However, we have discovered that TMSI is selective in the reaction with substrates containing both hydroxyl and ester functional groups towards dehydroxylation. For example, it was unexpected to observe that the methyl ester in compound of formula 9 was not cleaved when treated with TMSI. Rather it gave dehydroxylation product Clopidogrel of formula 1 in high yields and in good purity.

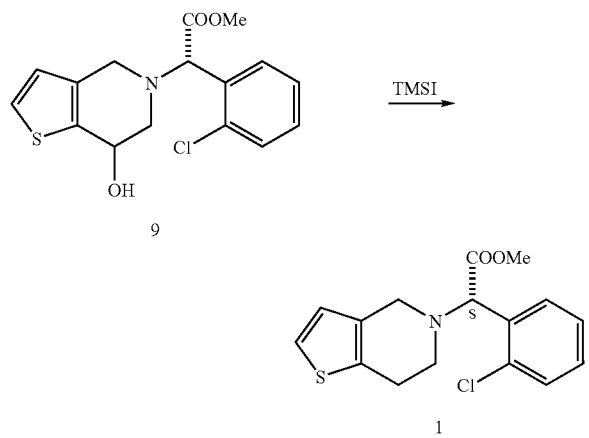

9

1

Furthermore, the formation of other possible by-products resulting from the use of TMSI in reactions with benzylic alcohols that have been reported previously such as iodide formation (J. Org. Chem., 1979, 44, 1247) or dimerization products (Tetrahedron, 1995, 51, 11043) have not been observed when the novel process of the instant invention is employed.

Iodosilane, for example TMSI, can be employed directly in the reaction or can be generated in situ in the reaction between chlorosilanes of formula $Si(R_4)_3Cl$, for example chlorotrimethylsilane (TMSCl), and sodium iodide (J. Org. Chem., 1979, 44, 1247) (Scheme 4). Again, $R_4$ can be an alkyl, alkenyl, alkynyl, aromatic group, or combinations thereof. This results in a less expensive alternative to utilizing TMSI obtained from a commercial source.

Scheme 4

TMSCl + NaI ⟶ TMSI + NaCl.

Furthermore, other iodosilanes (e.g. iodotriethylsilane) may be used directly in the reaction or be formed in situ from the corresponding chlorosilane and NaI.

Further details of the invention are illustrated by reference to the following non-limiting examples:

EXAMPLE 1

Methyl(S)-α-(4,5,6,7-tetrahydro-5-thieno[3,2-c]pyridyl)-o-chlorophenylacetate (1)

To a mixture of sodium iodide in acetonitrile is added chlorotrimethylsilane. The mixture is stirred at room temperature under nitrogen for 30 minutes. A solution of (αS, 7RS)-methyl-α-(7-hydroxy-4,5,6,7-tetrahydro-5-thieno[3, 2-c]pyridyl)-o-chlorophenylacetate (9) (23.4 g, 69.3 mmol) in toluene and acetonitrile is added to the mixture at 0–5° C. After the addition is complete the mixture is warmed to room temperature and stirred for 2 hours. Water is then added to the mixture at 0–5° C. The mixture is then warmed again to room temperature and stirred for an additional 4 hours. The reaction mixture is then basified with aqueous sodium bicarbonate solution. The organic layer is then washed with aqueous sodium thiosulfate solution, followed by water, then brine. The organic layer is then dried, filtered and concentrated to provide clopidogrel free base as an oil product (21.4 g). $^1$H-NMR ($CDCl_3$, ppm) 7.7 (1H, dd), 7.35 (1H, m), 7.2–7.35 (2H, m), 7.2 (1H, d), 6.68 (1H, dd), 4.95 (1H, s) 3.5–4.0 (2H, m), 3.75 (3H, s), 2.9 (4H, s); chiral HPLC 99:1 enantiomeric ratio.

EXAMPLE 2

Methyl(S)-α-(4,5,6,7-tetrahydro-5-thieno[3,2-c]pyridyl)-o-chlorophenylacetate (1)

To a mixture of sodium iodide in acetonitrile is added chlorotrimethylsilane. The mixture is stirred at room temperature under nitrogen for 1 hour. (αS,7RS)-methyl-α-(7-hydroxy-4,5,6,7-tetrahydro-5-thieno[3,2-c]pyridyl)-o-chlorophenylacetate bisulfate salt (30.0 g, 68.9 mmol) is added to the mixture at 0–5° C. After the addition is complete the mixture is warmed to room temperature and stirred for 8 hours. The reaction mixture is then basified with aqueous sodium bicarbonate solution. The organic layer is then washed with aqueous sodium thiosulfate solution, followed by water, then brine. The organic layer is then dried, filtered and concentrated to provide clopidogrel free base as an oily

EXAMPLE 3

Methyl(S)-α-(4,5,6,7-tetrahydro-5-thieno[3,2-c]pyridyl)-o-chlorophenylacetate (1)

To a mixture of sodium iodide in acetonitrile is added chlorotrimethylsilane. The mixture is stirred at room temperature under nitrogen for 1 hour. (αS,7RS)-methyl-α-(7-hydroxy-4,5,6,7-tetrahydro-5-thieno[3,2-c]pyridyl)-o-chlorophenylacetate hydrochloride salt (10.0 g, 26.7 mmol) is added to the mixture at 0–5° C. After the addition is complete the mixture is warmed to room temperature and stirred for 18 hours. The reaction mixture is then basified with aqueous sodium bicarbonate solution. The organic layer is then washed with aqueous sodium thiosulfate solution, followed by water, then brine. The organic layer is then dried, filtered and concentrated to provide clopidogrel free base as an oily product (8.10 g). The product obtained was found to be identical to the product obtained in Example 1 by $^1$H-NMR.

EXAMPLE 4

Methyl(S)-α-(4,5,6,7-tetrahydro-5-thieno[3,2-c]pyridyl)-o-chlorophenylacetate (1)

To a mixture of sodium iodide in acetonitrile is added chlorotrimethylsilane. The mixture is stirred at room temperature under nitrogen for 1 hour. (αS,7RS)-methyl-α-(7-hydroxy-4,5,6,7-tetrahydro-5-thieno[3,2-c]pyridyl)-o-chlorophenylacetate para toluenesulfonic acid salt (55.0 g, 108 mmol) is added to the mixture at 0–5° C. After the addition is complete the mixture is warmed to room temperature and stirred for 17 hours. The reaction mixture is then basified with aqueous sodium bicarbonate solution. The organic layer is then washed with aqueous sodium thiosulfate solution, followed by water, then brine. The organic layer is then dried, filtered and concentrated to provide clopidogrel free base as an oily product (30.6 g). The product obtained was found to be identical to the product obtained in Example 1 by $^1$H-NMR.

EXAMPLE 5

Methyl(S)-α-(4,5,6,7-tetrahydro-5-thieno[3,2-c]pyridyl)-o-chlorophenylacetate (1)

To a mixture of sodium iodide in acetonitrile, and in N,N,dimethylformamide is added chlorotriethylsilane. The mixture is stirred at room temperature under nitrogen for 1 hour. (αS,7RS)-methyl-α-(7-hydroxy-4,5,6,7-tetrahydro-5-thieno[3,2-c]pyridyl)-o-chlorophenylacetate bisulfate salt (30.2 g, 69.3 mmol) is added to the mixture at 0–5° C. After the addition is complete the mixture is warmed to room temperature and stirred for 12 hours. The reaction mixture is then basified with aqueous sodium bicarbonate solution. The organic layer is then washed with aqueous sodium thiosulfate solution, followed by water, then brine. The organic layer is then dried, filtered and concentrated to provide clopidogrel free base as an oily product (20.1 g). The product obtained was found to be identical to the product obtained in Example 1 by $^1$H-NMR.

product (21.4 g). The product obtained was found to be identical to the product obtained in Example 1 by $^1$H-NMR.

EXAMPLE 6

Methyl(S)-α-(4,5,6,7-tetrahydro-5-thieno[3,2-c]pyridyl)-o-chlorophenylacetate (1)

To a mixture of sodium iodide in acetonitrile, and acetone is added chlorotriethylsilane. The mixture is stirred at room temperature under nitrogen for 1 hour. (αS,7RS)-methyl-α-(7-hydroxy-4,5,6,7-tetrahydro-5-thieno[3,2-c]pyridyl)-o-chlorophenylacetate bisulfate salt 25.0 g, 66.8 mmol) is added to the mixture at 0–5° C. After the addition is complete the mixture is warmed to room temperature and stirred for 12 hours. The reaction mixture is then basified with aqueous sodium bicarbonate solution. The organic layer is then washed with aqueous sodium thiosulfate solution, followed by water, then brine. The organic layer is then dried, filtered and concentrated to provide clopidogrel free base as an oily product (20.6 g). The product obtained was found to be identical to the product obtained in Example 1 by $^1$H-NMR.

EXAMPLE 7

Methyl(S)-α-(4,5,6,7-tetrahydro-5-thieno[3,2-c]pyridyl)-o-chlorophenylacetate (1)

To a mixture of sodium iodide in dichloromethane is added chlorotriethylsilane. The mixture is stirred at room temperature under nitrogen for 90 min. A solution of (αS, 7RS)-methyl-α-(7-hydroxy-4,5,6,7-tetrahydro-5-thieno[3,2-c]pyridyl)-o-chlorophenylacetate (9) (8.2 g, 24.3 mmol) in dichloromethane is added to the mixture at 0–5° C. After the addition is complete the mixture is warmed to room temperature and stirred for 3 hours. Water is then added to the mixture at 0–5° C. The reaction mixture is then basified with aqueous sodium bicarbonate solution. The organic layer is then washed with aqueous sodium thiosulfate solution, followed by water, then brine. The organic layer is then dried, filtered and concentrated to provide clopidogrel free base as an oily product (6.69 g). The product obtained was found to be identical to the product obtained in Example 1 by $^1$H-NMR.

EXAMPLE 8

Methyl(S)-α-(4,5,6,7-tetrahydro-5-thieno[3,2-c]pyridyl)-o-chlorophenylacetate (1)

A solution of (αS,7RS)-methyl-α-(7-hydroxy-4,5,6,7-tetrahydro-5-thieno[3,2-c]pyridyl)-o-chlorophenylacetate (9) (59.79 g, 177.0 mmol) in toluene and acetonitrile is added to a solution of iodotrimethylsilane in acetonitrile at 0–5° C. After the addition is complete the mixture is warmed to room temperature and stirred for 2 hours. Water is then added to the mixture at 0–5° C. The mixture is then warmed again to room temperature and stirred for an additional 4 hours. The reaction mixture is then basified with aqueous sodium bicarbonate solution. The organic layer is then washed with aqueous sodium thiosulfate solution, followed by water, then brine. The organic layer is then dried, filtered and concentrated to provide clopidogrel free base as an oil product (55.8 g). The product obtained was found to be identical to the product obtained in Example 1 by $^1$H-NMR.

While the foregoing provides a detailed description of a preferred embodiment of the invention, it is to be understood that this description is illustrative only of the principles of the invention and not limitative. Furthermore, as many changes can be made to the invention without departing from the scope of the invention, it is intended that all material contained herein be interpreted as illustrative of the invention and not in a limiting sense.

The embodiments of the invention in which an exclusive property or privilege is claimed are as follows:

1. A process for the preparation of tetrahydrothieno[3,2-c]pyridine compound of formula 6:

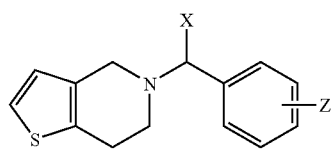

6 or their pharmaceutically acceptable salts, wherein the meaning of X is carboxyl, alkoxycarbonyl, aryloxycarbonyl, or carbamoyl of formula

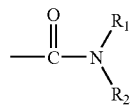

wherein $R_1$ and $R_2$ can be individually or simultaneously hydrogen, or alkyl; Z can be hydrogen, halogen, alkyl, aryl, aryloxy or alkoxy group, the process comprising conducting a dehydroxylation reaction on the compound of formula 5 in order to obtain a compound of formula 6, wherein said dehydroxylation reaction is effected by iodosilane represented by the formula $Si(R_3)_3I$, wherein $R_3$ selected from an alkyl,

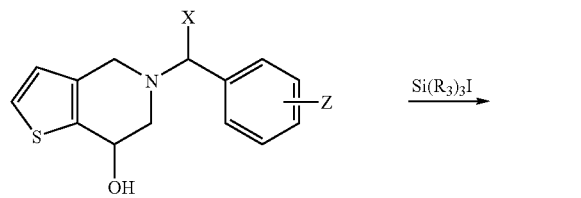

5

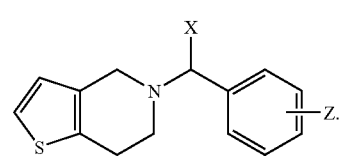

6

2. The process of claim 1 wherein said iodosilane is iodotrimethylsilane (TMSI).

3. The process of claim 1 or 2 wherein said iodosilane is generated in situ in the reaction between chlorosilanes of formula $Si(R_4)_3Cl$ and sodium iodide, wherein $R_4$ is selected from an alkyl, alkenyl, alkynyl, or aromatic group.

4. The process of claim 3 wherein said chlorosilanes is chlorotrimethylsilane.

5. The process of claim 1 wherein the compound of formula 6 is racemic or enantiomerically enriched Clopidogrel or pharmaceutical salts thereof.

6. The process of claim 1 or 2 wherein the compound of formula 5 is in a free base form or in a salt form.

7. The process of claim 1 wherein the reaction is conducted under a polar aprotic solvent, an aromatic solvent, or mixtures thereof.

8. The process of claim 7 wherein the polar aprotic solvent is selected from acetonitrile, $CH_2Cl_2$, N,N'-dimethylformamide and combinations thereof.

9. The process of claim 7 wherein the aromatic solvent is toluene.

10. A process for the preparation of compound of formula 1 or its pharmaceutically acceptable salts thereof, comprising conducting a dehydroxylation reaction on the compound of formula 9 or its salts thereof, wherein said dehydroxylation reaction is effected by iodotrimethylsilane (TMSI)

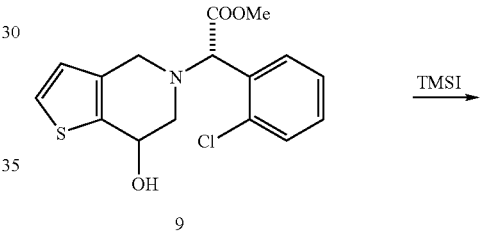

9

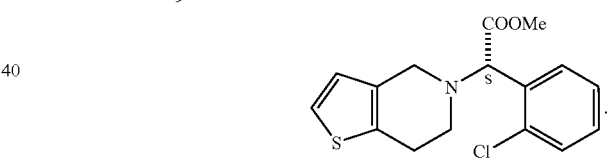

1

11. The process of claim 10 wherein the reaction is conducted under a polar aprotic solvent, an aromatic solvent, or mixtures thereof.

12. The process of claim 11 wherein the polar aprotic solvent is selected from acetonitrile, $CH_2Cl_2$, N,N'-dimethylformamide and combinations thereof.

13. The process of claim 11 wherein the aromatic solvent is toluene.

* * * * *